US011279208B2

(12) United States Patent
Iliffe-Moon et al.

(10) Patent No.: US 11,279,208 B2
(45) Date of Patent: Mar. 22, 2022

(54) CARTRIDGE AND A SYSTEM FOR SCENT DISPENSING AND A VEHICLE COMPRISING A SCENT DISPENSING SYSTEM

(71) Applicant: Bayerische Motoren Werke Aktiengesellschaft, Munich (DE)

(72) Inventors: Etienne Iliffe-Moon, Menlo Park, CA (US); Brian Mok, Santa Clara, CA (US)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 121 days.

(21) Appl. No.: 16/722,613

(22) Filed: Dec. 20, 2019

(65) Prior Publication Data
US 2021/0188047 A1    Jun. 24, 2021

(51) Int. Cl.
*A61L 9/12* (2006.01)
*B60H 3/00* (2006.01)

(52) U.S. Cl.
CPC .............. *B60H 3/0028* (2013.01); *A61L 9/12* (2013.01); *A61L 2209/133* (2013.01); *A61L 2209/134* (2013.01); *B60H 2003/0042* (2013.01)

(58) Field of Classification Search
CPC ...... A61L 9/12; A61L 9/122; A61L 2209/133; A61L 2209/134; B60H 3/0028; B60H 3/0035; B60H 2003/0042
See application file for complete search history.

(56) References Cited

U.S. PATENT DOCUMENTS

| 5,071,621 A * | 12/1991 | Tokuhiro | B60H 1/00764 422/4 |
| 8,448,739 B2 * | 5/2013 | Kolich | B60H 3/0007 180/271 |
| 10,537,653 B2 * | 1/2020 | Kelsen | A61L 9/14 |
| 10,596,293 B2 * | 3/2020 | Hsiao | B01D 35/30 |
| 2018/0318461 A1 * | 11/2018 | Nishimaki | A61L 9/122 |

FOREIGN PATENT DOCUMENTS

| EP | 1184083 A1 | 3/2002 | |
| WO | WO-2015052215 A1 * | 4/2015 | ........... B60H 3/0007 |
| WO | 2018022562 A1 | 2/2018 | |
| WO | 2019030771 A1 | 2/2019 | |
| WO | 2019154328 A1 | 8/2019 | |

OTHER PUBLICATIONS

Machine Translation of WO2015/052215A1 (Year: 2015).*

* cited by examiner

*Primary Examiner* — Timothy C Cleveland
(74) *Attorney, Agent, or Firm* — 2SPL Patent Attorneys PartG mbB; Kieran O'Leary

(57) ABSTRACT

Embodiments generally relate to a cartridge and a system for scent dispensing and a vehicle comprising a scent dispensing system. In particular, embodiments relate to a concept for a scent dispensing cartridge. A replaceable cartridge for a scent dispensing system comprises one or more chambers for storing scent media, a chamber having an air inlet and an air outlet that allows air to flow through the chamber; and one or more valves to prevent air from flowing through the one or more chambers.

18 Claims, 4 Drawing Sheets

CARTRIDGE AND A SYSTEM FOR SCENT DISPENSING AND A VEHICLE COMPRISING A SCENT DISPENSING SYSTEM

FIELD

Embodiments generally relate to a cartridge and a system for scent dispensing and a vehicle comprising a scent dispensing system. In particular, embodiments relate to a concept for a scent dispensing cartridge.

BACKGROUND

The human body is affected by its sense of smell. Leveraging a person's sense of smell can cause both physiological and psychological effects. It can also affect the sensory system as a whole. A smell can alter a person's emotion, mood, memory, and perception. And, in turn, how a person perceives a smell can be influenced by the other senses in interesting ways.

Many industries, including the automotive industry, have only slowly incorporated a sense experience into their products or have done so on a very basic level. Common problems with scent dispensing apparatuses include the over delivery of scents, the delivery of singular scents, and the delivery of only a limited number of fragrances. Additionally, these dispensers, also known as air fresheners, are not designed for the automotive application. Hence, there may be a desire for an improved scent dispensing apparatus that can deliver a richer sensory experience.

SUMMARY

Embodiments in the present disclosure relate to a cartridge for a scent dispensing apparatus. According to an embodiment, a replaceable cartridge for a scent dispensing system comprises one or more chambers for storing scent media. A chamber has an air inlet and an air outlet that allows air to flow through the chamber. The cartridge further comprises one or more valves to prevent air from flowing through the one or more chambers.

The valves may, for example, allow the cartridge to work in environmental conditions that might otherwise cause a scent leakage. A valve that provides a physical seal can prevent leakage of scent molecules and turn off or block airflow. If a cartridge has more than one chamber, a further chamber can be viewed as a separate channel that can be controlled independently, in combination, or in parallel. Additionally, by localizing the valves in the cartridge, sealed connections to other components might not be required.

The valves in a cartridge may prevent the leakage of scent during the manufacturing, production, and packaging process. Cartridges with valves may also reduce the amount of packaging or eliminate the need to have sealed packaging for the individual cartridges or the set of cartridges. Cartridges with valves may also improve a customer's or user's experience by minimizing the packaging a customer has to deal with before and after use, simplifying the un-packaging process, and making the installation of the cartridge easier.

According to another embodiment, the previously described replaceable cartridge further comprises an airflow source configured to generate an airflow through at least one chamber.

The airflow source provides airflow directly to the cartridge independent from other systems. An airflow source contained within the cartridge may allow the cartridge to be connected to other components that do not have active airflow or without sealed connections.

The replaceable cartridge may comprise multiple chambers and multiple airflow sources for the multiple chambers. Having multiple airflow sources may allow setting independent airflows for one or more chambers.

The replaceable cartridge may include at least one empty chamber for generating a scent-neutral airflow component. A scent-neutral component may help flush stray scent molecules from the device without introducing additional scents. The scent-neutral component may be used to accelerate the dissipation of a scent present in the environment, whether or not it was initially dispensed by the cartridge/apparatus. It may also be used in conjunction with the delivery of a scent from a cartridge to augment the scent in a way, potentially by diluting a scent and moving or dissipating the scent into the surrounding ambient air. This may help avoid olfactory adaptation or olfactory fatigue, which is a phenomenon that results in the temporary inability to distinguish a particular odor after prolonged exposure to it.

Additionally, air may be ventilated through an empty chamber without scent media. This ventilation may be activated alone or in combination with airflow through one or more chambers. The ventilation may purge or clean a system of any residual scent, increase the aeration of the scent stream, or increase the airflow before, during, or after a scent release. This ventilation carries the scent away from the device and increases scent diffusion and dissipation.

The replaceable cartridge may include inlet valves at the air inlet and outlet valves at the air outlet. In automotive applications, the environmental conditions can be such that scent cartridges may leak scents. This can be improved by sealing the scent cartridges with valves that provide a physical seal, and turning off or blocking the airflow.

The scent media of the previously described replaceable cartridge may be made up at least one element of the group of a gel-based substrate, a polymer-based substrate, a solid material, a bead-like material, and a liquid absorbing or holding material. A scent media made partially or entirely of a solid-state format may better withstand extreme environmental conditions, such as extreme temperature and humidity.

According to another embodiment, the replaceable cartridge may comprise a body having an exterior and an interior, the interior defining a channel in fluid connection with an at least one inlet aperture and an at least one outlet aperture from the exterior of the body to the channel. The channel comprises at least one chamber and the channel extends between the one or more valves. Each valve comprises at least one inlet sealing member and an at least one outlet sealing member. At least one inlet sealing member is located between the at least one inlet aperture and the at least one chamber and at least one outlet sealing member is located between the at least one chamber and the at least one outlet aperture. The sealing members have at least positions comprising an open position and a closed position. Sealing members might not be 100% open or closed but may have variable positions such as 25%, 50%, 75% or 100% open, or any value between 0% and 100%. Sealing members are arranged so that an airflow is enabled from the exterior of the body through the channel and return to the exterior when the at least one inlet or outlet sealing member are in the open position and the airflow is disabled through the channel when at least one of the inlet or outlet sealing member is in the closed position. A chamber comprises at least one solid-state scent medium. The solid-state scent medium is unable to pass through the at least one inlet aperture and the at least one outlet aperture and is unable to interfere with a transition of the at least one inlet or outlet sealing member between the open position and the closed position.

A replaceable cartridge may better withstand extreme environments, automotive or otherwise with sealing members located between the inlet and outlet apertures. The sealing members prevent air from flowing through the chamber and scent media or scent molecules from exiting the chamber. However, the sealing members should be arranged so that the scent media cannot interfere with the operation of the valves as they transition from an open to a closed position. This may be important for environments that experience extreme effects, such as within an automobile. The scent media in an automobile may experience forces in all directions, making it more likely for the media to escape than in a stationary environment. Further, the extreme temperature and humidity effects that may be present in an environment like an automobile may change the structure of the scent media (i.e. separation of the scent formula, evaporating the scent media or making it more pliable). The replaceable cartridge described better isolates the scent media from these effects to preserve the integrity of the scent media. It also contains any results of these environmental effects, and allows for better control of the release of the scent into the environment.

An inlet sealing member and an outlet sealing member may be in connection so that the position of the inlet sealing member corresponds with the position of the outlet sealing member. This allows for the simultaneous and instant adjusting of the inlet and outlet sealing members. This may allow for a simpler mechanical, electrical, or computational structure to open both valves simultaneously.

A replaceable cartridge may comprise an at least one chamber containing at least one element of the group of an anti-bacterial, a disinfectant, an odor treatment, or an odor neutralization media. These media may act to remove odors from the atmosphere or environment outside the cartridge. They may also act to cleanse or deodorize any system that the cartridge is connected or decontaminate valves or other components in connection with the chamber that may become contaminated with scent molecules. Decontaminating the cartridge or a system the cartridge is connected to may improve the operation of the cartridge's mechanical components by removing gunk or other debris that interfering with the cartridge's operation. This may prolong the life of the cartridge and prevent the unwanted leakage of scents from the suboptimal operation of the cartridge, particularly its valves. Additionally, deodorizing the cartridge or the surrounding atmosphere and environment may cause the scent that is dispensed from the cartridge to be more readily perceived. This may result in the overall reduction in scent delivered for a user to perceive the scent, prolonging the life of the cartridge and the scent media contained within it.

The previously described replaceable cartridge can be part of a scent dispensing system. The system may have at least one airflow source configured to generate an airflow through at least one chamber of the cartridge. The system may have a controller coupled to the at least one airflow source and is configured to control the airflow source and one or more valves to generate a mixture outside of the cartridge from an at least one airflow through the cartridge. A cartridge may be part of a system, such as a heating, ventilation, and air conditioning (HVAC) system where the airflow source is external to the cartridge. The system may be configured to operate the valves of the cartridge to control the dispersal of a scent. A cartridge that is part of a wider system allows for the interoperability of a cartridge with many form factors and streamline the production of the cartridge by allowing it to use prearranged airflow sources while still providing for a controlled scent dispersal in a suitable environment.

The at least one airflow in the previously described scent dispensing system comprises scented air and the cartridge is the last point of exit of the scented air. This creates a system that does not require a mixing element. An additional mixing element may create a contamination point that reduces the quality of the scented air and causes it to be contaminated with previously dispensed scents inadvertently. By making the cartridge the last point of exit of the scented air the scent is released directly into the environment without contaminating the released scent or interfering with other systems that may be negatively affected by either the scent molecules or any residue they may cause.

The replaceable cartridge in the previously described scent dispensing system may further comprise a combination of one or more chambers, one or more valves, and one or more outlets. This allows for multiple scents to be controlled independently in the scent dispensing system. Allowing for finer control over which scent is dispensed, in what manner, in what amount, and how it mixes with other scents.

The replaceable cartridge is removably insertable into the previously described scent dispensing system. The removability of the cartridge allows cartridges to be replaced allowing for new scent experiences without the replacement of the entire scent dispensing system.

A vehicle may comprise the previously described scent dispensing system. A vehicle may be any type of land-, sea-, and air-based vehicle or transportation system. The scent dispensing system, as described, may be particularly well suited to the extreme environments present in many land-, sea-, and air-based vehicles.

The previously described scent dispensing system is integrated into a heating, ventilation, and air conditioning system of the previously described vehicle. Integration into existing vehicle systems allows for the system to control the dispersal of a scent using existing airflow systems, as well as allowing the scent to be adjusted using additional elements like the heating, ventilation, and air conditioning systems. This may prolong a scent, disperse a scent, dissipate, neutralize, or remove a scent (such that it can no longer be smelled), adjust the character of a scent, or allow multiple scents to better intermix, creating new scent experiences.

The previously described scent dispensing system in a vehicle is controlled by one or more elements of the group of a vehicle operation status component (i.e. the vehicle's onboard computer that provides basic/core vehicle system info like speed, gear selection, lighting, etc.) a navigation or traffic component, an infotainment component, communication component, weather information, safety monitoring component, and an autonomous driving system component. This allows for the cartridge to be integrated with other external systems that can adjust and inform the perception of the smell released by the cartridge. For instance, using weather information could allow the system to attune scent based on humidity, temperature, or other aspects of the weather. Also, using infotainment could allow the scent to be adjusted to coincide with other sensory effects, such as music or video, heightening the users' perception of a scent.

BRIEF DESCRIPTION OF THE DRAWINGS

Some embodiments of apparatuses and systems will be described in the following only by way of example and with reference to the accompanying figures, in which.

DETAILED DESCRIPTION

Various embodiments will now be described more fully with reference to the accompanying drawings in which some embodiments are illustrated. The thicknesses of lines, layers, and/or regions in the figures may be exaggerated for clarity.

Accordingly, while further embodiments are capable of various modifications and alternative forms, some particular embodiments thereof are shown in the figures and will subsequently be described in detail. However, this detailed description does not limit further embodiments to the particular forms described. Further embodiments may cover all modifications, equivalents, and alternatives falling within the scope of the disclosure. Same or like numbers refer to like or similar elements throughout the description of the figures, which may be implemented identically or in modified form when compared to one another while providing for the same or similar functionality.

It will be understood that when an element is referred to as being "connected" or "coupled" to another element, the elements may be directly connected or coupled via one or more intervening elements. If two elements A and B are combined using an "or", this is to be understood to disclose all possible combinations (i.e. only A, only B, as well as A and B) if not explicitly or implicitly defined otherwise. An alternative wording for the same combinations is "at least one of A and B" or "A and/or B". The same applies, mutatis mutandis, for combinations of more than two elements.

The terminology used herein for the purpose of describing particular embodiments is not intended to be limiting for further embodiments. Whenever a singular form such as "a," "an" and "the" is used, and using only a single element is neither explicitly or implicitly defined as being mandatory, further embodiments may also use plural elements to implement the same functionality. Likewise, when a functionality is subsequently described as being implemented using multiple elements, further embodiments may implement the same functionality using a single element or processing entity. It will be further understood that the terms "comprises," "comprising," "includes" and/or "including," when used specify the presence of the stated features, integers, steps, operations, processes, acts, elements, and/or components but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the embodiments belong.

Figure 1:
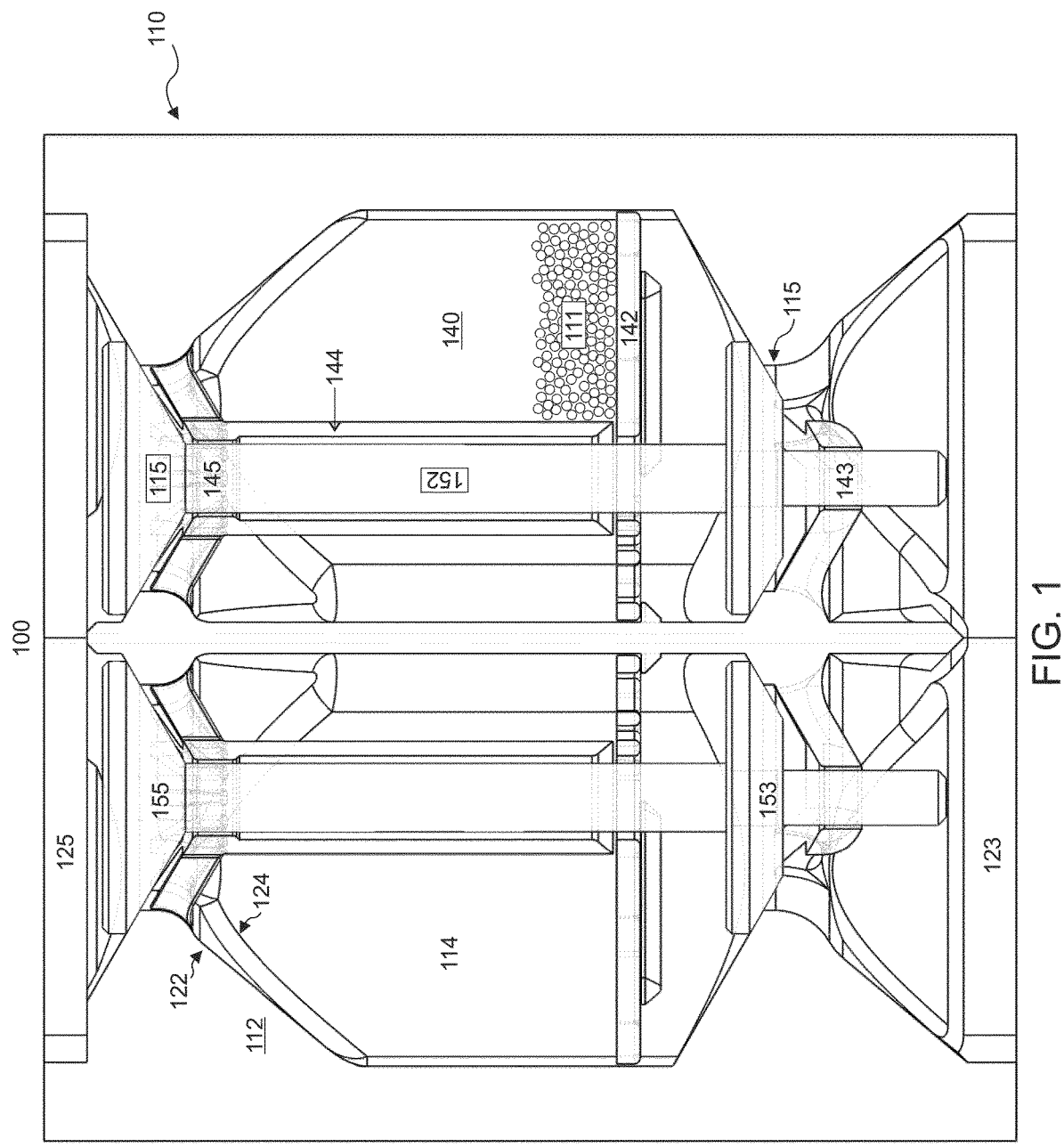
FIG. 1 shows a cross-sectional view of an embodiment of a cartridge.

FIG. 1 is a cross-section of the elements of a replaceable cartridge 110 for a scent dispensing system 100. The replaceable cartridge 110 comprises one or more chambers 140 for storing scent media 111. A chamber 140 has an air inlet 143 and an air outlet 145 that allows air to flow through the chamber 140. The cartridge 110 also comprises one or more valves 115 to prevent air from flowing through the one or more chambers 140.

A valve 115 may be any element that regulates, directs, or controls the flow of a fluid, namely air, by opening, closing, or partially obstructing the flow of a fluid through the inlet 143 or outlet 145 of the chamber 140. In the embodiment in FIG. 1 the valves 115 are linear motion valves but a valve may also be a rotary motion, quarter-turn valve, sliding valve, or any combination or mechanism that sufficiently seals the cartridge 210. In an open configuration, a valve 115 allows fluid to flow in a direction from higher pressure to lower pressure. In a closed configuration a valve 115 works to prevent the entry of air into the cartridge and to prevent the escape of scent molecules from the cartridge 110. In the embodiment shown in FIG. 1 the valves are implemented using one or more pushrod valves, which use disks or sealing members 153, 155 that seal an opening in a seating. The disc is attached to a rod. As can be seen from FIG. 1, two discs can be attached to a single rod or shaft, forming a connection 152 that allows for sealing/opening the inlet 143 and the outlet 145 simultaneously. As will be detailed subsequently the rod may be actuated or moved by an actuator. The connection may also be a screw, a belt, an electrical connection, or any connection that links the valves. It is not required to have a set of valves for the inlet and outlet. Outlet adjacent valves 115, either adjacent to the outlet of the cartridge 125 or a chamber 145, may suffice if other mechanisms prevent the leakage of scent media, such as positive air pressure at the inlet of the cartridge and a filter, grate, mesh, or another containment device 142 that allows air to pass through the chamber 140 but not the scent media 111. Scent media 111 may include other media for aerosolization, diffusion, or dispersion from the cartridge 110, such as media to remove an odor or scent from the environment or otherwise cleanse, filter, or disinfect the atmosphere or environment outside the cartridge 210. The replaceable cartridge may comprise an at least one chamber containing at least one element of the group of an antibacterial, a disinfectant, an odor treatment, or an odor neutralization media.

The chamber 145 may be configured to isolate scent 111 or other media from any moving components (e.g. the connection 152 rod or shaft that connects the valves 115). For example, there may be a wall 144 or another containment mechanism that separates the scent media 111 from the connection 152. Containing and isolating the scent media 111 prevents leakage of residue and the possibility that residue can interfere, gum up, or contaminate moving or running surfaces causing any mechanical movement to become slow, sticky, or otherwise prevent smooth mechanical movement.

The cartridge 110 can be produced using any conventional manufacturing technique, including casting and molding, machining, joining, shearing and forming. It may also be formed using additive manufacturing systems and techniques, often referred to as three dimensional (3D) fabrication or 3D printing. The cartridge 110 can be made from metals, wood or paper, polymers, or any material, a combination of materials, or a composite material that can sufficiently store scent media without leakage. The use of biodegradable materials, such as wood or paper, may aid with the disposal of the replaceable cartridge 110 in an environmentally-friendly way.

The term replaceable means that the cartridge may be conveniently added to or removed from the system 100 according to the user's needs. A replaceable cartridge may be interchanged with a different replaceable cartridge (e.g. comprising different scent media or different embodiments as described in this application). A different cartridge added to the system may serve a different function depending on its scent media or configuration. Further, a producer of replaceable cartridges may be able to tailor several different versions of the cartridge to provide a curated scent experience to the user. Each replaceable cartridge may also comprise a method of identification so that when it is removably inserted into the system 100 the system can identify the cartridge, its configuration, and contents. Additionally, replaceable nature of the cartridge, it is possible for a user to purchase a system 100 without a cartridge if it does not meet their present needs and then add the cartridge to the system 100 when it better suits the user.

The valves 115 may be oriented at the inlet 123 and outlet 125 of the cartridge 110 or at the inlet 143 or outlet 145 of one or more chambers 140 within the cartridge 110. In the embodiment in FIG. 1, the cartridge comprises inlet apertures 123, 143 and outlet apertures 125,145. These inlets and outlets may be constructed in any manner that allows air to pass through chamber 140. For example, inlets 123, 143, and outlets 125, 145 may be constructed as injection ports, slits, funnels, sieves, other openings, or a combination of opening types. At least one of the pair of inlet and outlet valves 115 may float enough to accommodate potential manufacturing tolerances, and use a spring (e.g. a metal spring or plastic molded feature, etc.) or similar mechanical force to engage the floating valve. This allows for one of the valves 115 to be actuated and for the actuated valve to dictate the position (i.e. open or closed) of the floating valve.

The replaceable cartridge's scent media 111 may comprise a gel-based substrate, a polymer-based substrate, a solid material, a bead-like material, and a liquid absorbing or holding material. Additionally, a scent can be mixed in with a 3D printing substance to form a printing filament. The filament can then be printed to form a 3D printed scent media. Another alternative would be to print a 3D matrix from a filament that comprises a scent absorbing material, then introducing the scent to the printed structure to form a scent media.

In some embodiments, the replaceable cartridge 110 may comprise at least one empty chamber 140 for generating a scent-neutral airflow component. Passing air through at least one empty chamber 140 may purge or clean the system of any residual scent, increase the aeration of the scent stream, or increase the airflow (e.g. before, during, or after a scent release) to carry the scent away from the cartridge 110 and increase scent diffusion and dissipation. The ventilation of air through an empty chamber 140 may be activated alone or in combination with airflow through one or more additional chambers 140.

FIG. 1 further illustrates the replaceable cartridge comprising a body 112 having an exterior 122 and an interior 124, the interior defining a channel 114 in fluid connection with an at least one inlet aperture 123 and an at least one outlet aperture 125 from the exterior 122 of the body 112 to the channel 114. The channel 114 comprises at least one chamber 140 that extends between the one or more valves 115. The one or more valves 115 comprise an at least one inlet sealing member 153 and an at least one outlet sealing 155. The at least one inlet sealing member 153 is located between the at least one inlet aperture 123 and the at least one chamber 140. The at least one outlet sealing member 155 is located between the at least one chamber 140 and the at least one outlet aperture 125. Further, the at least one inlet sealing member 153 and the at least one outlet sealing member 155 have positions at least comprising an open position and a closed position. The at least one inlet and outlet sealing members 153, 155 are arranged so that an airflow is enabled from the exterior 122 of the body 112 through the channel 114 and return to the exterior 122 when the at least one inlet and/or outlet sealing members 153, 155 are in the open position and the airflow is disabled through the channel 114 when at least one of the inlet and/or outlet sealing members 153, 155 is in the closed position.

Within the at least one chamber 140 may be at least one solid-state scent medium 111. The solid-state scent medium 111 is unable to pass through the at least one inlet aperture 123 and the at least one outlet aperture 125. Additionally, the solid-state scent medium 111 is unable to interfere with a transition of the at least one inlet or outlet sealing member 153, 155 between the open position and the closed position.

FIG. 1 also shows the replaceable cartridge where the inlet sealing member 153 and the outlet sealing member 155 are in connection 152 so that the position of the inlet sealing member 153 corresponds with the position of the outlet sealing member 155. The inlet 153 and outlet sealing members 155 may be mechanically connected or mechanically independent. The inlet 153 and outlet sealing members 155 may operate simultaneously or independently.

The corresponding positions of the sealing members 153, 155 may not be identical. Operating conditions and manufacturing tolerances may allow for some inconsistency in the valve positions. The sealing members 153, 155 may be composed of a rubber or elastomeric material with enough compliance to take up the likely manufacturing tolerance and provide a sufficient seal. These materials may also reduce noise from the engagement of the valves.

Particularly, FIG. 1 shows a singular embodiment of a cartridge 110 for a scent dispensing system 100. The cartridge 110 comprises a plurality of chambers 140 containing an at least one scent media 111. The chambers 140 are sealed at their inlet aperture 143 and outlet aperture 145 by valves 115. The valves 115 located adjacent to inlets 143 of the chambers 140 have inlet sealing members or disks 153 adapted to shape of the inlets 143 to create an air-tight seal. Similarly, the valves 115 located adjacent to the outlets 143 of the chambers 140 are similarly adapted to create an air-tight seal. Optionally, each pair of inlet and outlet valves 115 for each chamber 140 are linked by a connection 152 rod. This connection 152 extends in this embodiment through the inlet sealing member 153 toward the cartridge inlet 123. This allows for the connection to be actuated opening and closing the pair of sealing members 153, 155 simultaneously. The connection 152 and chamber inlet and outlet 143, 145 are formed in such a way that it still allows air to pass through the chamber. An optional containment device 142 or grate 142 prevents the scent media 111 from interfering with the operation of the inlet sealing member 153 or exiting the inlet aperture 143. The orientation of the connection 153 and chamber outlet 145 similarly do not allow for the passage of the scent media 111 from interfering with the operation of the outlet sealing member 155 or exiting the inlet aperture 145.

In this embodiment, actuation of a pair of valves 115 for a chamber 140—the valves 115 having an inlet sealing member 153 and outlet sealing member 155—allows air to pass through the cartridge inlet 123 into the chamber 140, and pick up the scent of the scent media 111. The scented air then exits the chamber 140 through the chamber outlet 145 and further exits the cartridge 110 through the cartridge outlet 125. The flow of air is halted when at least one sealing member 153, 155 of the pair for each chamber is actuated to the closed position.

Figure 2:
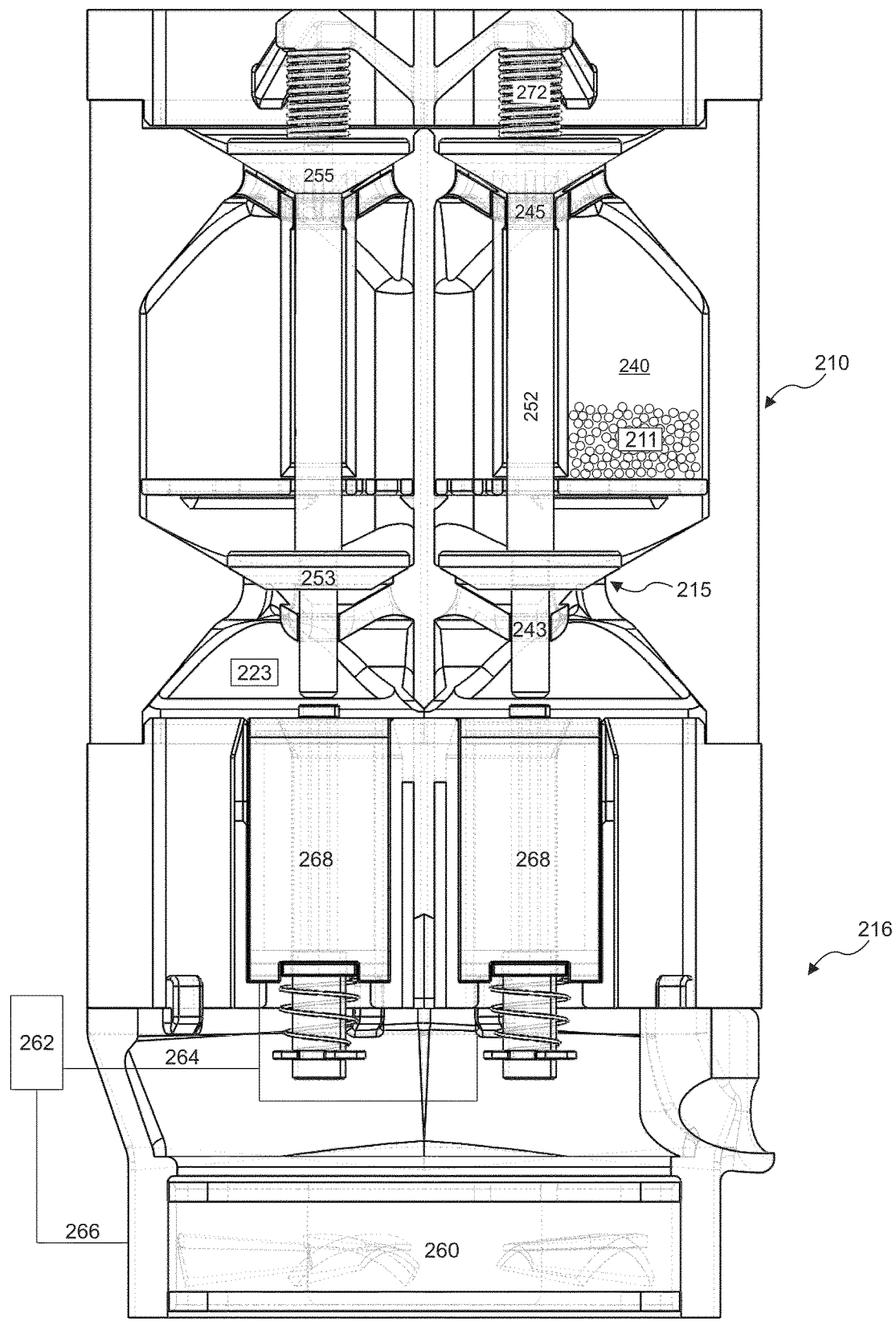
FIG. 2 shows a cross-sectional view of an embodiment of the scent dispensing system with the cartridge.

FIG. 2 shows a cross-section of the elements of a replaceable cartridge 210 for a scent dispensing system 200. The replaceable cartridge 210 comprises one or more chambers 240 for storing scent media 211. A chamber 240 has an air inlet 243 and an air outlet 245 that allows air to flow through the chamber 240. The cartridge 210 also comprises one or more valves 215 to prevent air from flowing through the one or more chambers 240. The replaceable cartridge 210 further comprises an airflow source 260 configured to generate an airflow through at least one chamber 240.

An airflow source 260 may be one or more fans, pumps, compressors, or any devices configured to generate airflow. The source may provide airflow to the inlets 243 of individual chambers 240 or to the inlet 223 of the cartridge 210. Embodiments include a single airflow source 260 per cartridge 210 or a number of airflow sources 260 for some or all of the chambers 240 of the cartridge 210. Airflow sources 260 are on the inlet side, not the outlet, so not to be contaminated by the scented air as it exits the system 200.

The replaceable cartridge 210 may comprise multiple chambers 240 and multiple airflow sources 260 for the multiple chambers 240. There may be one airflow source 260 for one chamber or multiple chambers. Additionally, there may be multiple airflow sources 260, for a single chamber. For example if an HVAC system is used in conjunction with a fan to boost the flow of air through the cartridge 210.

FIG. 2 also shows a scent dispensing system 200 comprising the replaceable cartridge 210 and at least one airflow source 260, which is configured to generate an airflow through at least one chamber 240. FIG. 2 further shows a controller 262, which is coupled 266 to at least one airflow source 266 and is configured to control the at least one airflow source 260 and the one or more valves 215 to generate a mixture of a first airflow through the cartridge and a second airflow directly outside the cartridge. The replaceable cartridge 210 may comprise a combination of one or more chambers 240, one or more valves 215, and one or more outlets 245. Valves 215 may be configured to be driven (e.g. open or closed) based on the air pressure present on the inlet side of their sealing members 253 if the air has sufficient pressure to overcome a mechanical arrangement (e.g. valve-spring arrangement). Different valve pairs (i.e. inlet and outlet) in the cartridge 210 may be driven at different pressures so that specific scents in specific chambers 240 are released by adjusting the air pressure produced by the airflow source 260.

A scent dispensing system 200 may stand alone or may be supplied or sold as an "optional accessory", a "factory installed" accessory or option, a dealer-installed accessory or an accessory installed by the customer or third party. The system 200 may connect to a vehicle or other apparatus for power (e.g. electrical connection, wireless charging, etc.) for data that may be provided wired or wireless (e.g. Bluetooth, WIFI, etc.). The system could be located in a specifically designed location, receptacle or port, or be located in a pre-existing receptacle such as a cup holder, ashtray, armrest or glove box.

FIG. 2 also shows the controller 262 coupled 264 to at least one actuator 268 to control the one or more valves 215 of the cartridge 210. In examples the controller 262 may be implemented using one or more processing units, one or more processing devices, any means for processing, such as a processor, a computer or a programmable hardware component being operable with accordingly adapted software. In other words, the described functions of the controller may as well be implemented in software, which is then executed on one or more programmable hardware components. Such hardware components may comprise a general-purpose processor, a Digital Signal Processor (DSP), a micro-controller, on an electronic control unit (ECU), etc.

The systems 200 may comprise an apparatus 216 that is adapted to receive a replaceable cartridge 210 in such a way that replaceable cartridge 210 is removably insertable into the system 200. When the removable cartridge 210 is inserted into the system 100 it might not require any physical coupling to the actuator 268 to operate. FIG. 2 demonstrates that the connection 252 between the inlet sealing member 253 and the outlet sealing member 255 of the valves 215 is not physically connected to the actuator 268. However, the operation of the actuator is such that it can operate the connection 252 while still allowing the cartridge 210 to be removed.

A replaceable cartridge 210 may be disposable or recyclable. A recyclable cartridge may be composed of recyclable materials that can be deposed into a user's recycling system or they may be returned to the manufacturer so that they can be refilled and reused.

The apparatus 216 may comprise at least one airflow source 260 and actuator 268. An actuator 268 may be a gear, electric, pneumatic, hydraulic, or solenoid actuator adapted to the type of valve or valves it actuates. Common examples of actuators that may be used include an electric motor (i.e. electro-mechanical, such as a motor connected to a geared, cam, or screw arrangement), servo motor, bimetallic actuator, or memory alloy actuator. The controller 262 for the system 200 may be located within the apparatus 216 or be external to the apparatus 216. The controller may be any electronic device, including a processor that is configured to control any airflow source 260 and actuators 260 of the system 200. The cartridge 210 may include features to allow for silent operation or reduce the mechanical noise of the valves 215 or actuator 268 opening and closing. This may be done with the addition of damping material (e.g. rubber or elastomer stops or the valves' 215 surfaces being made in a soft, rubber or elastomeric material).

The scent dispensing system shown in FIG. 2 produces a scented airflow within the cartridge 210. The scented airflow then exits the cartridge 210 and enters the surrounding environment. In this figure, the cartridge 210 is the last point of exit of the scented air from the system 200.

Specifically, FIG. 2 shows a singular embodiment of a scent dispensing system 200 comprising a cartridge 210 as described above in FIG. 1. The system also comprises an apparatus 216 comprising actuators 268 and an airflow source 260. The apparatus may also comprise springs 272 or other components to hold the valves 215 of cartridge 210 in a closed position until they are actuated open by the actuators 268. The actuators 268 and airflow source 260 of the apparatus 216 may be connected to an external controller 262 via electronic connections 264 and 266.

Figure 3:
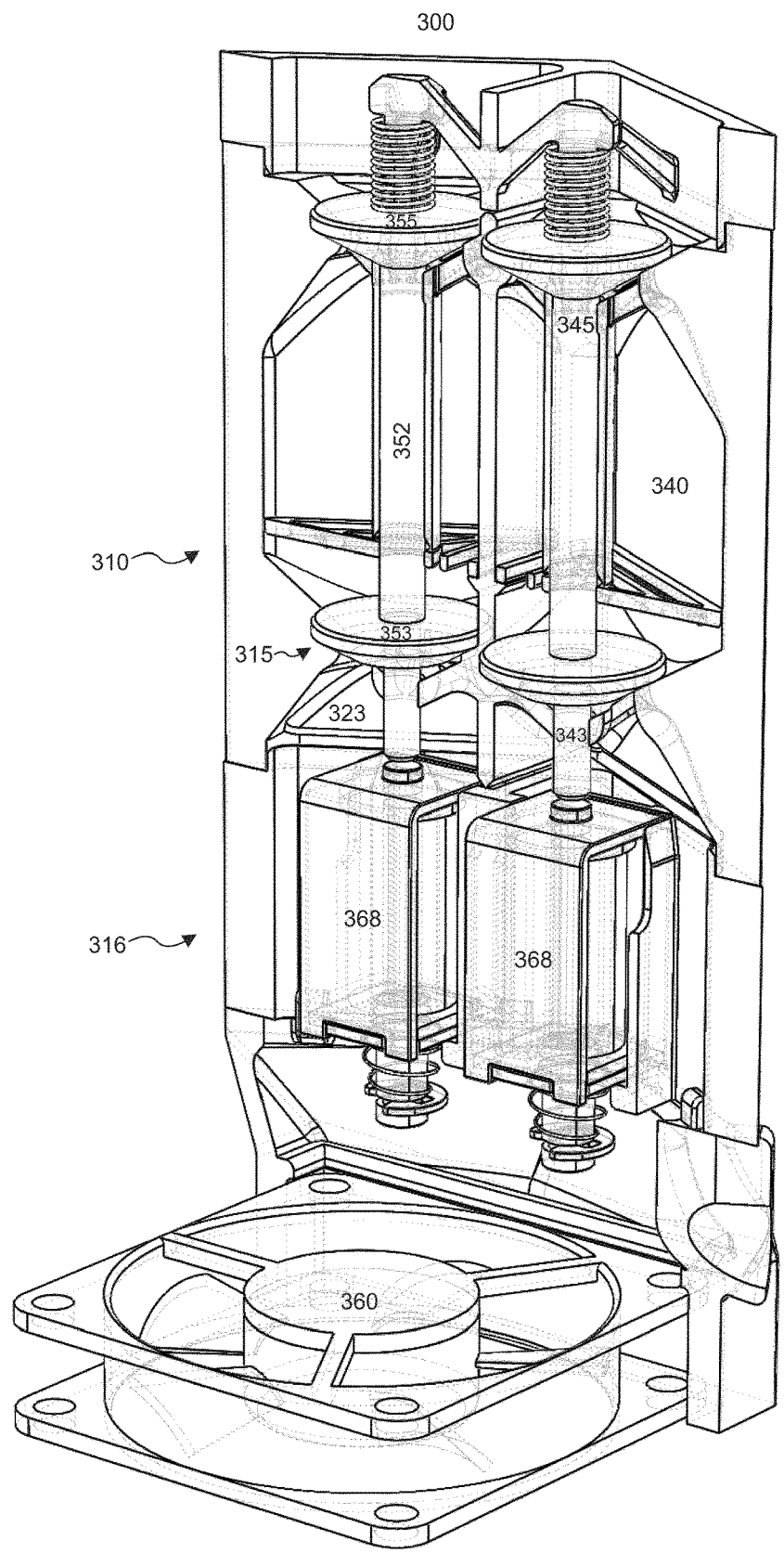
FIG. 3 shows three-dimensional cross-sectional view of and embodiment of the cartridge and system.

FIG. 3 shows a three-dimensional view of the cartridge 310 and system 300. The replaceable cartridge 310 may include all the features of the system 300, including the apparatus 316. The cartridge shown in the figure may include a chamber 340 with an at least one inlet 343 and an outlet 345 aperture or opening. The valves 315 comprise either inlet 353 or outlet 355 sealing members that, in the closed position, may prevent the escape of scent molecules from the chamber 340. The inlet 353 and outlet 355 sealing members may be connected 352 (e.g. mechanically, electrically, or otherwise) so that the position of the inlet sealing member 353 corresponds with the position of the outlet sealing member 355. The apparatus 316, as shown in the figure, may include at least one airflow source 360 and an at least one actuator 368 that controls the position of at least one valve 315.

Figure 4:
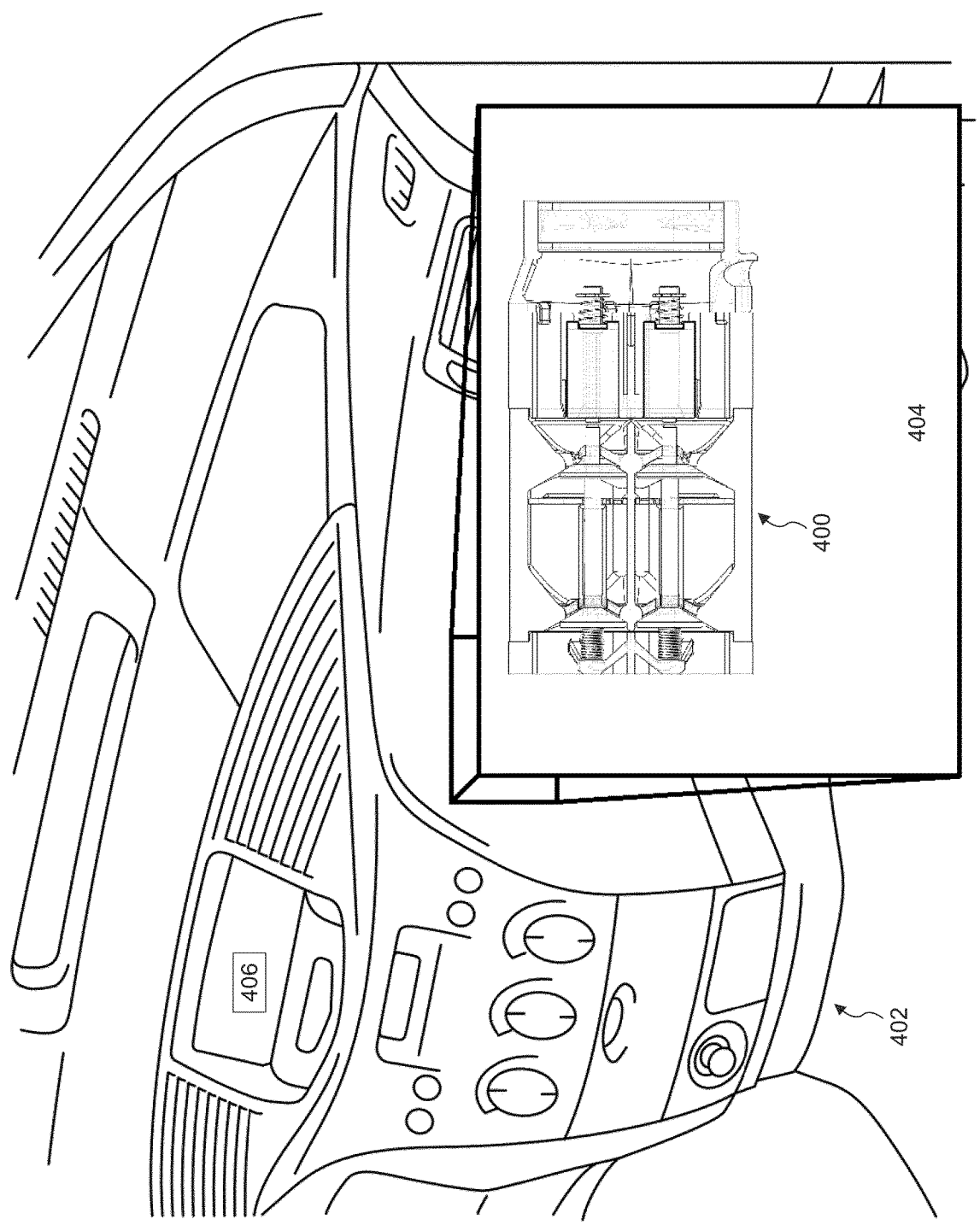
FIG. 4 shows a view of an embodiment of the cartridge and system within a vehicle.

FIG. 4 shows a vehicle 402 comprising a scent dispensing system 400. The figure shows the system 400 integrated into a vehicle's heating, ventilation, and air conditioning system 404. FIG. 4 also shows the system 400 controlled by one or more elements of the group of a vehicle operation/status component, navigation/traffic component, an infotainment component, weather information, safety monitoring component, and an autonomous driving system component 406.

A vehicle may be land-, sea-, or air-based. It may include any apparatus used for transportation. Additionally, the system is vehicle independent and may be deployed in environments and systems not used or designed for transportation, such as in a home, a retail environment, public spaces, an office or any of the climate systems that operate in those spaces.

The aspects and features mentioned and described together with one or more of the previously detailed embodiments and figures, may as well be combined with one or more of the other embodiments to replace a like feature of the other embodiment or to additionally introduce the feature to the other embodiment.

What is claimed is:

1. A replaceable cartridge for a scent dispensing system, the cartridge comprising:
    a plurality of chambers for storing scent media, wherein the plurality of chambers are arranged in parallel,
        each of the chambers having a longitudinal axis, and comprises an air inlet at an anterior end and an air outlet at a posterior end of the longitudinal axis,
            wherein the air inlet and the air outlet enable air to flow through each of the plurality of chambers from the anterior end to the posterior end; and
    one or more valves to prevent air from flowing through the plurality of chambers.

2. The replaceable cartridge of claim 1, further comprising an airflow source, which is configured to generate an airflow through at least one-chamber of the plurality chambers.

3. The replaceable cartridge of claim 1, comprising a plurality of airflow sources, wherein each of the plurality of airflow sources is configured to generate an airflow through a subset of the plurality of chambers.

4. The replaceable cartridge of claim 3, further comprising an at least one empty chamber for generating a scent-neutral airflow component.

5. The replaceable cartridge of claim 1, wherein a plurality of the one or more valves comprise a subset of inlet valves and a subset of outlet valves, wherein each chamber of the plurality of chambers comprises an inlet valve of the subset of inlet valves at the air inlet and an outlet valve of the subset of outlet valves at the air outlet.

6. The replaceable cartridge of claim 1, wherein the scent media comprises at least one element of the group of a gel-based substrate, a polymer-based substrate, a solid material, a bead-like material, and a liquid absorbing or holding material.

7. The replaceable cartridge of claim 5 further comprising:
    a body having an exterior and an interior and further comprising an at least one inlet aperture and an at least one outlet aperture located at a periphery of the body bridging the exterior and interior, wherein:
        the interior defines a channel in fluid connection with the at least one inlet aperture and the at least one outlet aperture enabling air to flow through the body;
        wherein the channel comprises the plurality of chambers arranged in parallel;
        wherein the subset of inlet valves is located within the channel between the inlet aperture and each air inlet of the plurality of chambers, and
        wherein the subset of outlet valves is located within the channel between each air outlet of the plurality of chambers and the outlet aperture;
    wherein each of the subset of inlet valves comprise an at least one inlet sealing member and each of the subset of outlet valves comprise an at least one outlet sealing member;
        wherein the at least one inlet sealing member and the at least one outlet sealing member have at least positions comprising an open position and a closed position;
        wherein the at least one inlet sealing member and the at least one outlet sealing member are arranged so that an airflow is enabled from the exterior of the body through the corresponding chamber and return to the exterior when the at least one inlet sealing member and the at least one outlet sealing member are in the open position and the airflow is disabled through the corresponding chamber when the at least one inlet sealing member and/or the at least one outlet sealing member is in the closed position;
    the plurality of chambers comprising at least one solid-state scent medium per chamber;
        wherein the at least one solid-state scent medium is unable to pass through the at least one air inlet and the at least one air outlet of the corresponding chamber; and
        wherein the at least one solid-state scent medium is unable to interfere with a transition of the at least one inlet sealing member or the at least one outlet sealing member of the corresponding chamber as the transition is made between the open position and the closed position.

8. The replaceable cartridge of claim 7, wherein the at least one inlet sealing member and the at least one outlet sealing member of each corresponding chamber are in connection so that the position of the at least one inlet sealing member corresponds with the position of the at least one outlet sealing member.

9. The replaceable cartridge of claim 3, wherein a plurality of chambers comprise an at least one unscented chamber, wherein the at least one unscented chamber comprises at least one element of the group of an anti-bacterial, a disinfectant, an odor treatment, or an odor neutralization media.

10. A scent dispensing system comprising:
    the replaceable cartridge of claim 1;
    at least one airflow source, which is configured to generate an airflow through the plurality of chambers;
    a controller, which is coupled to the at least one airflow source and which is configured to control the at least one airflow source and the one or more valves to generate an airflow through the replaceable cartridge.

11. The scent dispensing system of claim 10, wherein wherein a plurality of the one or more valves of the replaceable cartridge comprise a subset of inlet valves, wherein each chamber of the plurality of chambers comprises an inlet valve of the subset of inlet valves at the air inlet.

12. The scent dispensing system of claim 10, wherein the replaceable cartridge is removably insertable into the system.

13. The scent dispensing system of claim 11 wherein the control of the subset of inlet valves is executed using an at least one actuator proximate to the anterior ends of the plurality of chambers.

14. A vehicle comprising the scent dispensing system of claim 10.

15. The vehicle of claim 14, wherein the scent dispensing system is integrated into a heating, ventilation, and air conditioning system.

16. The vehicle of claim 14, wherein the scent dispensing system is controlled by one or more elements of the group of a navigation/traffic component, an infotainment component, weather information, safety monitoring component, and an autonomous driving system component.

17. The replaceable cartridge of claim 5, wherein the inlet valve and the outlet valve of each chamber are connected by a rod, wherein the rod substantially extends along or tangentially to the longitudinal axis.

18. The replaceable cartridge of claim 17 wherein the rod passes through the corresponding chamber of the cartridge to connect the inlet valve and the outlet valve.

* * * * *

UNITED STATES PATENT AND TRADEMARK OFFICE
CERTIFICATE OF CORRECTION

| | |
|---|---|
| PATENT NO. | : 11,279,208 B2 |
| APPLICATION NO. | : 16/722613 |
| DATED | : March 22, 2022 |
| INVENTOR(S) | : Etienne Iliffe-Moon and Brian Mok |

It is certified that error appears in the above-identified patent and that said Letters Patent is hereby corrected as shown below:

In the Claims

Column 12, Line 60 (Claim 11), please strike "wherein" as this word is repeated back-to-back.

Signed and Sealed this
Twenty-eighth Day of June, 2022

Katherine Kelly Vidal
*Director of the United States Patent and Trademark Office*